US007790827B2

(12) United States Patent
Nguyen et al.

(10) Patent No.: US 7,790,827 B2
(45) Date of Patent: Sep. 7, 2010

(54) SILICONE POLYETHER-AMIDE BLOCK COPOLYMERS

(75) Inventors: Kimmai Thi Nguyen, Midland, MI (US); Lenin James Petroff, Bay City, MI (US); Maria Pretzer, Midland, MI (US); Michael Starch, Midland, MI (US); Kenneth Zimmerman, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 11/664,572

(22) PCT Filed: Nov. 28, 2005

(86) PCT No.: PCT/US2005/042858
§ 371 (c)(1),
(2), (4) Date: Apr. 3, 2007

(87) PCT Pub. No.: WO2006/060295
PCT Pub. Date: Jun. 8, 2006

(65) Prior Publication Data
US 2008/0045687 A1    Feb. 21, 2008

Related U.S. Application Data

(60) Provisional application No. 60/632,061, filed on Dec. 1, 2004.

(51) Int. Cl.
*C08G 77/22* (2006.01)
(52) U.S. Cl. .............................. 528/15; 528/26; 528/28; 424/401
(58) Field of Classification Search ................... 528/15, 528/25–26, 28, 31, 33; 424/401
See application file for complete search history.

(56) References Cited

U.S. PATENT DOCUMENTS

| 3,419,593 A | 12/1968 | Willing |
| 3,715,334 A | 2/1973 | Karstedt |
| 3,814,730 A | 6/1974 | Karstedt |
| 3,923,705 A | 12/1975 | Smith |
| 4,127,494 A * | 11/1978 | Lindenberger ............... 252/77 |
| 5,175,325 A | 12/1992 | Brown et al. |
| 5,874,069 A | 2/1999 | Mendolia et al. |
| 5,919,441 A | 7/1999 | Mendolia et al. |
| 5,981,680 A | 11/1999 | Petroff et al. |
| 6,051,216 A | 4/2000 | Barr et al. |
| 6,242,509 B1 * | 6/2001 | Berger et al. ................. 523/122 |
| 6,362,288 B1 | 3/2002 | Brewer et al. |
| 6,800,713 B2 | 10/2004 | Cook et al. |
| 6,916,464 B2 | 7/2005 | Hansenne et al. |
| 6,958,155 B2 | 10/2005 | Lu et al. |
| 7,160,979 B2 * | 1/2007 | Nataniel et al. .......... 528/339.3 |
| 2003/0072730 A1 | 4/2003 | Tournilhac |
| 2003/0105260 A1 * | 6/2003 | Cook et al. .................... 528/10 |
| 2003/0170188 A1 | 9/2003 | Ferrari et al. |
| 2003/0232030 A1 | 12/2003 | Lu et al. |
| 2003/0235552 A1 | 12/2003 | Yu |
| 2003/0235553 A1 | 12/2003 | Lu et al. |
| 2004/0115154 A1 * | 6/2004 | Yu .......................... 424/70.12 |
| 2004/0120912 A1 | 6/2004 | Yu |
| 2004/0147670 A1 * | 7/2004 | Hupfield ..................... 524/588 |
| 2004/0156807 A1 * | 8/2004 | Lin et al. ................. 424/70.12 |
| 2004/0180032 A1 | 9/2004 | Manelski et al. |

FOREIGN PATENT DOCUMENTS

| EP | 1 266 647 A1 | 12/2002 |
| EP | 1 266 648 A1 | 12/2002 |
| EP | 1 266 653 A1 | 12/2002 |
| WO | WO 2004/054523 A1 | 7/2004 |
| WO | WO 2004/054524 A1 | 7/2004 |

OTHER PUBLICATIONS

Salamone, Joseph.C., Polymeric Materials Encyclopedia, Jul. 1996, CRC, 1 edition, p. 5916 (Polyether amide).*

* cited by examiner

*Primary Examiner*—Margaret G Moore
(74) *Attorney, Agent, or Firm*—Alan Zombeck

(57) ABSTRACT

Silicone block copolymers containing polyether-amide units, processes to prepare such silicone block copolymers, and their use in various personal care, cosmetic, household care, and healthcare formulations are disclosed.

11 Claims, No Drawings

SILICONE POLYETHER-AMIDE BLOCK COPOLYMERS

CROSS REFERENCE TO RELATED APPLICATIONS

This application is a U.S. national stage filing under 35 U.S.C. §371 of PCT Application No. PCT/US05/42858 filed on 28 Nov. 2005, currently pending, which claims the benefit of U.S. Provisional Patent Application No. 60/632,061 filed 1 Dec. 2004 under 35 U.S.C. §119 (e). PCT Application No. PCT/US05/42858 and U.S. Provisional Patent Application No. 60/632,061 are hereby incorporated by reference.

TECHNICAL FIELD

The present invention relates to silicone block copolymers containing polyether-amide units, processes to prepare such silicone block copolymers, and their use in various personal care, cosmetic, household care, and healthcare formulations. The silicone block copolymers are also useful as fabric and textile treatments as well as thermoplastic additives.

BACKGROUND

Silicone polyamide copolymers have found widespread use in various commercial formulations. In particular, silicone polyamide copolymers have found utility in personal care formulations for their ability to act as a "structuring" or "gelling" agent in a composition containing a silicone, especially volatile silicones. The following summarizes representative examples of such patent references.

U.S. Pat. No. 5,874,069 teaches a base composition and corresponding cosmetic composition which can be formed as solids (for example, gels or sticks) and which comprise a solvent which includes a silicone fluid (for example, a silicone oil such as cyclomethicone) and a thickening agent formed from a wax and a polyamide gellant wherein at least one of the wax and polyamide includes silicon-containing moieties.

U.S. Pat. No. 5,919,441 discloses compositions which comprises gelling agents which (1) contain both siloxane groups and hydrogen-bonding groups to thicken compositions containing silicone fluids (volatile and/or non-volatile silicone fluids); (2) are non-flowable solids at room temperature; and (3) dissolve in a fluid which contains silicone at a temperature of 25-250° C. to form a translucent or clear solution at a temperature in this range.

U.S. Pat. No. 6,051,216 disclose siloxane-based polyamides as gelling agents for cosmetic products, methods for making such agents, formulations thereof and cosmetic formulations therewith. The polyamides according to the '216 patent contain siloxane groups in the main chain and act to thicken compositions containing volatile and/or non-volatile silicone fluids.

While these references represent advances in the art, a need still exists for improved gelling agents. In particular there is a need to identify silicone based gelling or structuring agents for volatile siloxane based formulations where the silicone gelling agent is not as brittle as the silicone polyamide known in the art. There is also a need to identify silicone gelling agents having lower melt temperatures than the silicone polyamides known in the art, for improved personal care formulations. Furthermore, there is a need to identify improved silicone polyamide structuring/gelling agents have improved hydrophilicity which can allow improved formulation flexibility with polar solvents.

The present inventors have discovered certain silicone block copolymers containing polyether-amide units that solve the aforementioned needs.

SUMMARY

The present invention relates to a silicone block copolymer having at least one repeating polyether-amide unit represented by the formula

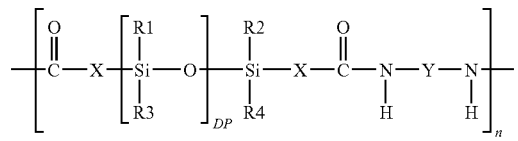

wherein
X is a linear or branched $C_1$-$C_{30}$ alkylene chain;
Y is a divalent organic group containing at least one polyoxyalkylene group having the formula —$(C_mH_{2m}O)_z$—, where m is 2 to 4 inclusive, z is 1 to 700,
$R^1$-$R^4$ are independently a monovalent organic group;
DP is an integer having a value of 1-500;
and n is an integer having a value of 1-500.

The present invention further relates to a process for making a silicone block copolymer comprising;
I) reacting an omega-olefinic carboxylic acid with a diamine containing at least one polyoxyalkylene group having the formula —$(C_mH_{2m}O)_z$—,
where m is 2 to 4 inclusive, z is 1 to 700 to form a vinyl endblocked diamide,
II) reacting the vinyl endblocked diamide with an SiH containing siloxane to form the silicone block copolymer.

The present invention further relates to the use of the silicone block copolymer in personal, household, health care formulations and applications, as well as their use in textile, fabric finishing formulations, and as thermoplastic additives.

DETAILED DESCRIPTION

The silicone block copolymers of the present invention have at least one repeating polyether-amide unit represented by the formula (Formula A);

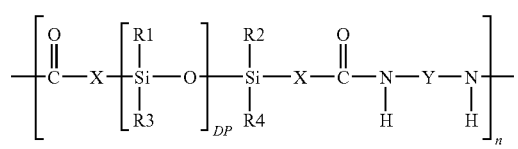

wherein
X is a linear or branched $C_1$-$C_{30}$ alkylene chain;
Y is a divalent organic group containing at least one polyoxyalkylene group having the formula —$(C_mH_{2m}O)_z$—, where m is 2 to 4 inclusive, z is 1 to 700,
$R^1$-$R^4$ are independently a monovalent organic group;
DP is an integer having a value of 1-500;
and n is an integer having a value of 1-500.

In Formula A, X is a linear or branched $C_1$-$C_{30}$ alkylene chain, thus X may be a divalent, aliphatic hydrocarbon group having 1-30 carbons, alternatively having 3-10 carbons, or alternatively having 10 carbons such as —$(CH_2)_{10}$—.

In Formula A, Y is a divalent organic group containing at least one polyoxyalkylene group having the formula —$(C_mH_{2m}O)_z$—, where m is 2 to 4 inclusive, z is 1 to 700, alternatively 1 to 100, or alternatively 1 to 20. The polyoxyalkylene group typically can comprise oxyethylene units —$(C_2H_4O)$—, oxypropylene units —$(C_3H_6O)$—, oxybutylene units —$(C_4H_8O)$—, or mixtures thereof. If more than one oxyalkylene group is present, the oxyalkylene units can be arranged in any fashion to form either a block or randomized copolymer structure, or alternatively form a randomized copolymer group. Typically, the polyoxyalkylene block comprises both oxyethylene units ($C_2H_4O$) and oxypropylene units ($C_3H_6O$). The polyoxyalkylene group may be bonded to each of the nitrogen atoms in Formula A via a divalent hydrocarbon group, which is typically an isopropylene group, —$CH(CH_3)CH_2$—, or ethylene group —$CH_2CH_2$—.

Each of $R^1$-$R^4$ in Formula A is independently selected from a monovalent organic group. These monovalent organic groups may have from 1 to 20 carbon atoms, alternatively 1 to 10 carbon atoms, and are exemplified by, but not limited to alkyl groups such as methyl, ethyl, propyl, butyl, pentyl, hexyl, heptyl, octyl, undecyl, and octadecyl; cycloalkyl such as cyclohexyl; aryl such as phenyl, tolyl, xylyl, benzyl, and 2-phenylethyl; and halogenated hydrocarbon groups such as 3,3,3-trifluoropropyl, 3-chloropropyl, and dichlorophenyl. At least 50 percent, alternatively at least 80%, of the organic groups in each of $R^1$-$R^4$ in Formula A may be methyl (denoted as Me). Typically, the siloxane block, as designated in Formula A as

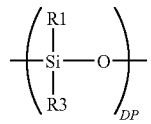

is a predominately linear polydimethylsiloxane having the formula $(Me_2SiO)_{DP}$, where DP is as defined below.

DP may range from 1 to 700, alternatively 7-500, or alternatively 7-150. In this context, DP represents an average value for degree of polymerization of the siloxane units as shown in Formula A with this average being a number average based on all the siloxane segments in all units of Formula A in the material considered.

In Formula A, the integer n may range from 1 to 500, alternatively 1-100, or alternatively 4-25.

If repeated with no variations in the defined variables, Formula A is representative of a linear block copolymer. Variations of the invention include: (1) polyamides in which multiple values of DP, and of units X, Y, and $R^1$-$R^4$ occur in one polymeric molecule, and wherein the sequencing of these units may be alternating, random or block; (2) polyamides in which an organic triamine or higher amine such as tris(2-aminoethyl)amine replaces the organic diamine in part during the preparation of the vinyl endblocked diamide, to produce a branched or crosslinked molecule; and (3) physical blends of any of (1) and (2) and/or linear copolymers.

The silicone block copolymers of the present invention may be illustrated by the following representative, non-limiting, structural formulas, where DP, z, and n are as defined above, EO represents the oxyethylene unit, PO represents the oxypropylene unit, and BO represents the oxybutylene unit;

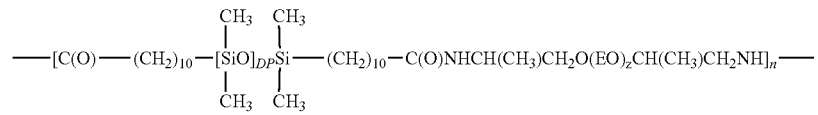

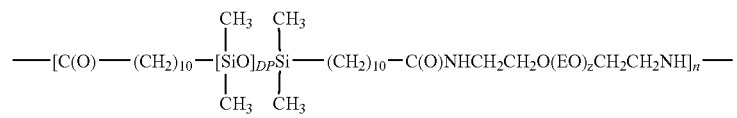

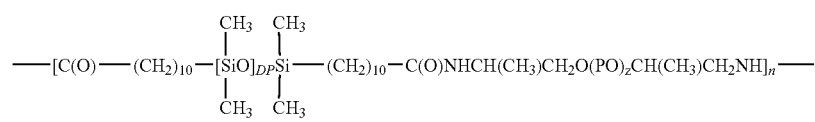

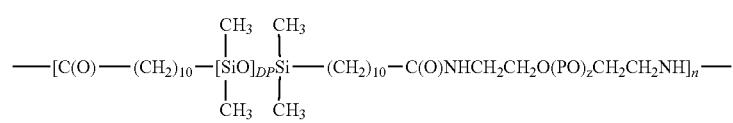

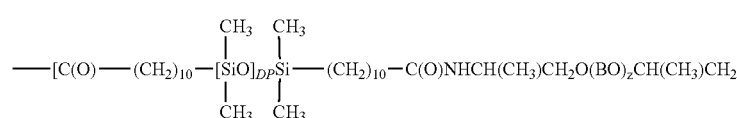

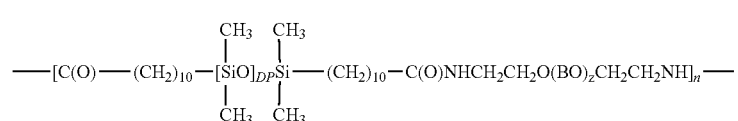

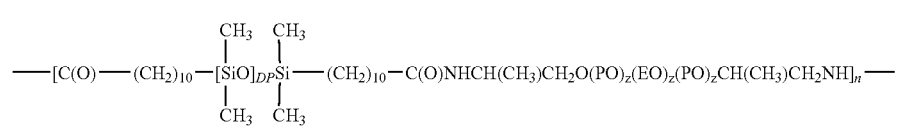

The silicone block copolymers may also contain additional "blocks" or units in its copolymer structure, or alternatively, in a terpolymer structure. These additional blocks may consist of additional alkylene, polyoxyalkenes, or organopolysiloxane units. These additional units may be incorporated into the silicone block copolymers by the use of the corresponding alpha omega olefin during its preparation. Suitable alpha omega olefins are described below.

The silicone block copolymers of the present invention may be prepared by any technique known in the art for preparing such block copolymers, but in particular, may be made by the procedures described in U.S. Pat. No. 6,800,713, which is incorporated herein by reference. When utilizing the procedures of the '713 patent, the silicone block copolymers of the present invention are prepared using polyether-diamines, which are described in more detail below.

The present invention further relates to a process for making a silicone block copolymer comprising;
I) reacting an omega-olefinic carboxylic acid with a diamine containing at least one polyoxyalkylene group having the formula $-(C_mH_{2m}O)_z-$,
where m is 2 to 4 inclusive, z is 1 to 700 to form a vinyl endblocked diamide,
II) reacting the vinyl endblocked diamide with an SiH containing siloxane to form the silicone block copolymer.

The first step of the process of the present invention involves the reaction of an olefinic acid with an organic diamine to produce a vinyl endblocked diamide. The reaction of step I) may be conducted in any manner and conditions which are known in the art to effect the formation of amides by reacting a carboxylic acid with an amine. Alternatively, the vinyl endblocked diamide may be a commercial product, and used directly in the present process.

The organic diamide is then in turn reacted with an SiH containing siloxane, such as a hydride-terminated polydimethylsiloxane having an average structure as the one depicted below:

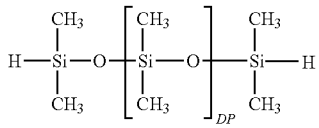

where DP is an integer having a value of 1-500, in the presence of a hydrosilylation catalyst to form a silicone block copolymer which includes at least one repeating unit represented by Formula A, described above.

Suitable omega-olefinic acids which can be used in step I) include undecylenic acid $H_2C=CH(CH_2)_8COOH$, acrylic acid $H_2C=CHCOOH$, 3-butenoic acid (vinylacetic acid) $H_2C=CHCH_2COOH$, 4-pentenoic acid $H_2C=CHCH_2CH_2COOH$, and other olefinic acids with carbon chains of varying length.

The diamines of step I, must contain at least one polyoxyalkylene group having the formula $-(C_mH_{2m}O)_z-$, where m is 2 to 4 inclusive, z is 1 to 700. The polyoxyalkylene-diamines are also commonly known as polyetherdiamines, and may be for example poly(oxyethylene)diamines or poly(oxypropylene)diamines. Polyoxyalkylene-diamines are known in the art, and many are commercially available. Representative, non-limiting examples of suitable polyoxyalkylene-diamines include; XTJ-502 Poly(oxyethylene) diamine [CAS 65605-36-9], XTJ-504 Triethyleneglycoldiamine [CAS 929-59-9], JEFFAMINE® HK-511 Polyetherdiamine [CAS 194673-87-5], JEFFAMINE® D-230 Polyoxypropylenediamine [CAS #9046-10-0], JEFFAMINE® D-400 POLYOXYPROPYLENEDIAMINE [CAS 9046-10-0], JEFFAMINE® D-2000 POLYOXYPROPYLENEDIAMINE [CAS 9046-10-0]. Additional representative, non-limiting examples of suitable polyoxyalkylene-diamines include the "*DPA—Series Ether Amines*" from Tomah (Tomah Products, Inc., Milton Wis.). This series of diamines is represented by the general formula; $H_2NCH_2CH_2CH_2-O-R-O-CH_2CH_2CH_2NH_2$, where O—R—O represents various glycol moieties, as indicated in parentheses in the following listing of commercial products;

DPA-PG (propylene glycol),
DPA-DPG (dipropylene glycol)
DPA-3PG (tripropylene glycol)
DPA-425 (poly(propylene glycol))
DPA-725 (poly(propylene glycol))
DPA-1000 (poly(propylene glycol))
DPA-1200 (poly(propylene glycol))
DPA-2000 (poly(propylene glycol))
DPA-4000 (poly(propylene glycol))
NDPA-10 (ethylene glycol))
DPA-DEG (diethylene glycol)
DPA-200E (poly(ethylene glycol))
DPA-400E (poly(ethylene glycol))
DPA-1000E (poly(ethylene glycol))
NDPA-11 (1,3-propane diol)
DPA-12 (2-methyl-1,3-propane diol)
NDPA-12 (1,4-butane diol)
IDPA-12 (1,3-butane diol)
NDPA-14 (1,6 hexane diol)
DPA-CHDM (cylclohexane-1,4-dimethanol)

A platinum catalyzed hydrosilylation reaction is typically used to effect the reaction in step II). Hydrosilylations are well known in the art and involves the reaction between a polysiloxane containing ≡Si—H groups, and a material containing unsaturation, e.g., vinyl groups. The reaction typically uses a catalyst to effect the reaction between the ≡SiH containing polysiloxane and the material containing unsaturation, i.e., the organic diamide in the case of the present invention. Suitable catalysts are Group VIII transition metals, i.e., the noble metals. Such noble metal catalysts are described in U.S. Pat. No. 3,923,705, incorporated herein by reference to show platinum catalysts. One preferred platinum catalyst is Karstedt's catalyst, which is described in Karstedt's U.S. Pat. Nos. 3,715,334 and 3,814,730, incorporated herein by reference. Karstedt's catalyst is a platinum divinyl tetramethyl disiloxane complex typically containing one weight percent of platinum in a solvent such as toluene. Another preferred platinum catalyst is a reaction product of chloroplatinic acid and an organosilicon compound containing terminal aliphatic unsaturation. It is described in U.S. Pat. No. 3,419,593, incorporated herein by reference. Most preferred as the catalyst is a neutralized complex of platinous chloride and divinyl tetramethyl disiloxane, for example as described in U.S. Pat. No. 5,175,325.

The noble metal catalyst can be used in an amount of from 0.00001-0.5 parts per 100 weight parts of the ≡SiH containing polysiloxane. Alternatively, the catalyst should be used in an amount sufficient to provide 5-15 parts per million (ppm) Pt metal per total composition.

Carrying out of the reaction of step II) is simply a matter of combining the ≡SiH containing polysiloxane(s), the material containing unsaturation, i.e., the organic diamide, and the catalyst; and mixing these ingredients. The reaction temperature can vary over a wide range, and the optimum temperature is dependent upon the concentration of the catalyst and the nature of the reactants. Ordinarily, it is best to keep the reaction temperature below 300° C. Best results with most reactants can be obtained by initiating the reaction at 80° C. to 180° C., and maintaining the reaction within reasonable limits of this range.

Typically, the process is carried out using approximately a 1:1 molar ratio of ≡Si—H containing polysiloxane and the material containing unsaturation. It is expected that useful materials may also be prepared by carrying out the process with an excess of either the ≡Si—H containing polysiloxane or the material containing unsaturation, but this would be considered a less efficient use of the materials. Typically, the material containing the unsaturation is used in slight excess to ensure all the SiH is consumed in the reaction.

The present invention further relates to a process for making a silicone block copolymer comprising;
I) reacting an omega-olefinic carboxylic acid with a diamine containing at least one polyoxyalkylene group having the formula —$(C_mH_{2m}O)_z$—,
where m is 2 to 4 inclusive, z is 1 to 700 to form a vinyl endblocked diamide,
II) reacting the vinyl endblocked diamide and an alpha-omega olefin with an SiH containing siloxane to form the silicone block copolymer. In this embodiment of the present invention, an alpha-omega olefin is added to step II) of the process, otherwise the techniques and procedures for performing steps I) and II) are the same as described above. As used herein, the alpha-omega olefin may be represented by the general formula $H_2C=CH$-A-$CH=CH_2$, where A represents a divalent organic group or organopolysiloxane. When A is a divalent organic group, it may be selected from linear or branched $C_1$-$C_{30}$ alkylene chains. Thus A may be a divalent, aliphatic hydrocarbon group having 1-30 carbons, particularly 3-10 carbons, and more particularly 4 carbons, for example 1, 5 hexadiene. A may also be a polyether (polyoxyalkylene) group, where the polyoxyalkylenes are as described above. A may also be an organopolysiloxane, and in particular a linear polydimethylsiloxane formula $(Me_2SiO)_{DP}$, where DP is as defined above. The alpha-omega olefin can be added in step II) for the purpose of altering the final chemical/physical properties of the resulting silicone block copolymer.

In a preferred embodiment of the process of the present invention, anyone or all of the starting materials, i.e. the carboxylic acid, diamines, alpha-omega olefin, and SiH siloxanes, are "processed" according to the teachings of U.S. Pat. No. 6,800,713 (which is incorporated by reference) to enhance copolymer formation.

The present invention further relates to the silicone block copolymers produced by the method described above.

The silicone block copolymers of the present invention can be used to form gels of either silicone or organic oils. The silicone can be any organopolysiloxane having the general formula $R_iSiO_{(4-i)/2}$ in which i has an average value of one to three and R is a monovalent organic group. The organopolysiloxane can be cyclic, linear, branched, and mixtures thereof.

In one embodiment, the silicone is a volatile methyl siloxane (VMS) which includes low molecular weight linear and cyclic volatile methyl siloxanes. Volatile methyl siloxanes conforming to the CTFA definition of cyclomethicones are considered to be within the definition of low molecular weight siloxane.

Linear VMS have the formula $(CH_3)_3SiO\{(CH_3)_2SiO\}_fSi(CH_3)_3$. The value of f is 0-7. Cyclic VMS have the formula $\{(CH_3)_2SiO\}_g$. The value of g is 3-6. Preferably, these volatile methyl siloxanes have a molecular weight of less than 1,000; a boiling point less than 250° C.; and a viscosity of 0.65 to 5.0 centistoke ($mm^2$/s), generally not greater than 5.0 centistoke ($mm^2$/s).

Representative linear volatile methyl siloxanes are hexamethyldisiloxane (MM) with a boiling point of 100° C., viscosity of 0.65 $mm^2$/s, and formula $Me_3SiOSiMe_3$; octamethyltrisiloxane (MDM) with a boiling point of 152° C., viscosity of 1.04 $mm^2$/s, and formula $Me_3SiOMe_2SiOSiMe_3$; decamethyltetrasiloxane ($MD_2M$) with a boiling point of 194° C., viscosity of 1.53 $mm^2$/s, and formula $Me_3SiO(Me_2SiO)_2SiMe_3$; dodecamethylpentasiloxane ($MD_3M$) with a boiling point of 229° C., viscosity of 2.06 $mm^2$/s, and formula $Me_3SiO(Me_2SiO)_3SiMe_3$; tetradecamethylhexasiloxane ($MD_4M$) with a boiling point of 245° C., viscosity of 2.63 $mm^2$/s, and formula $Me_3SiO(Me_2SiO)_4SiMe_3$; and hexadecamethylheptasiloxane ($MD_5M$) with a boiling point of 270° C., viscosity of 3.24 $mm^2$/s, and formula $Me_3SiO(Me_2SiO)_5SiMe_3$.

Representative cyclic volatile methyl siloxanes are hexamethylcyclotrisiloxane ($D_3$), a solid with a boiling point of 134° C., a molecular weight of 223, and formula $\{(Me_2)SiO\}_3$; octamethylcyclotetrasiloxane ($D_4$) with a boiling point of 176° C., viscosity of 2.3 $mm^2$/s, a molecular weight of 297, and formula $\{(Me_2)SiO\}_4$; decamethylcyclopentasiloxane ($D_5$) with a boiling point of 210° C., viscosity of 3.87 $mm^2$/s, a molecular weight of 371, and formula $\{(Me_2)SiO\}_5$; and dodecamethylcyclohexasiloxane ($D_6$) with a boiling point of 245° C., viscosity of 6.62 $mm^2$/s, a molecular weight of 445, and formula $\{(Me_2)SiO\}_6$.

The silicone can be any polydiorganosiloxane fluid, gum, or mixtures thereof. If the polyorganosiloxane has a molecular weight equal to or greater than 1000, it can be blended with the volatile methyl siloxanes described above. The polydiorganosiloxane gums suitable for the present invention are essentially composed of dimethylsiloxane units with the other units being represented by monomethylsiloxane, trimethylsiloxane, methylvinylsiloxane, methylethylsiloxane, diethylsiloxane, methylphenylsiloxane, diphenylsiloxane, ethylphenylsiloxane, vinylethylsiloxane, phenylvinylsiloxane, 3,3,3-trifluoropropylmethylsiloxane, dimethylphenylsiloxane, methylphenylvinylsiloxane, dimethylethylsiloxane, 3,3,3-trifluoropropyldimethylsiloxane, mono-3,3,3-trifluoropropylsiloxane, aminoalkylsiloxane, monophenylsiloxane, monovinylsiloxane and the like.

When an organic oil is used in the gel, it may be selected from any organic oil known in the art suitable for use in the preparation of personal, household, or healthcare formulations. Suitable organic oils include, but are not limited to, natural oils such as coconut oil; hydrocarbons such as mineral oil and hydrogenated polyisobutene; fatty alcohols such as octyldodecanol; esters such as C12-C15 alkyl benzoate; diesters such as propylene dipelarganate; and triesters, such as glyceryl trioctanoate. The organic oil components can also be mixture of low viscosity and high viscosity oils. Suitable low viscosity oils have a viscosity of 5 to 100 mPa·s at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or mixtures of octyldodecanol, acetylated lanolin alcohol, cetyl acetate, isododecanol, polyglyceryl-3-diisostearate, or mixtures thereof. The high viscosity surface oils generally have a viscosity of 200-1,000,000 mPa·s at 25° C., alternatively a viscosity of 100,000-250,000 mPa·s. Surface oils include castor oil, lanolin and lanolin derivatives, triisocetyl citrate, sorbitan sesquioleate, C10-18 triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or mixtures thereof. Mention may be made, among the optional other non-silicone fatty substances, of mineral oils, such as liquid paraffin or liquid petroleum, of animal oils, such as perhydrosqualene oil, or alternatively of vegetable oils, such as sweet almond, calophyllum, palm, castor, avocado, jojoba, olive or cereal germ oil. It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The organic oil may also be a volatile organic solvent. Suitable as a volatile organic solvent component are various C8-C20 isoparaffins such as C12 isoparaffin made by The Permethyl Corporation having the tradename Permethyl® 99A, or a C12 isoparaffin (isododecane). Various C16 isoparaffins commercially available, such as isohexadecane are also suitable. Other suitable volatile solvents are various fluoro containing materials such as Ethyl Perfluoroisobutyl Ether (and) Ethyl Perfluorobutyl Ether (3M Cosmetic fluid CF-76) and Cosmetic Fluid CF-61: Methyl Perfluoroisobutyl Ether (and) Methyl Perfluorobutyl Ether (3M Cosmetic Fluid CF-61).

The silicone block copolymers according to this present invention can be used in a variety of personal, household, and healthcare applications. In particular, the silicone block copolymers have utility as thickening agents in hair, skin, underarm, and cosmetic, product applications. The siloxane units provide compatibility with silicone fluids such as cyclomethicones, while the amide linkages and the spacing and selection of the locations of the amide linkages, facilitate thickening and formation of such products.

In particular, the silicone block copolymers of the present invention may be used: as thickening agents, as taught in U.S. Pat. Nos. 6,051,216, 5,919,441, 5,981,680; to structure oils, as disclosed in WO 2004/060271 and WO 2004/060101; in sunscreen compositions as taught in WO 2004/060276; as structuring agents in cosmetic compositions also containing film-forming resins, as disclosed in WO 03/105801; in the cosmetic compositions as taught in US Patent Application Publications 2003/0235553, 2003/0072730, 2003/0170188, EP 1,266,647, EP 1,266,648, EP1,266,653, WO 03/105789, WO 2004/000247 and WO 03/106614; as structuring agents as taught in WO 2004/054523; in long wearing cosmetic compositions as taught in US Patent Application Publication 2004/0180032; in transparent or translucent care and/or make up compositions as discussed in WO 2004/054524; all of which are incorporated herein by reference.

The silicone block copolymers can also be used as additives in various thermoplastic formulations, as for example taught in U.S. Pat. No. 6,362,288. The silicone block copolymers are also useful as textile and fabric treatments.

EXAMPLES

These examples are intended to illustrate the invention to one of ordinary skill in the art and are should not be interpreted as limiting the scope of the invention set forth in the claims. All tests were performed at 23° C., unless indicated otherwise.

The following etherdiamines were used in the Examples below to prepare etherdiamides.

| Etherdiamine | Commercial Supplier/name |
|---|---|
| $NH_2CH_2CH_2OCH_2CH_2OCH_2CH_2NH_2$ | Huntsman's XTJ-504 |
| $NH_2(CH_2)_3OCH_2CH_2OCH_2CH_2O(CH_2)_3NH_2$ | Tomah's DPA-DEG |
| $NH_2(CH_2)_3(OCH_2CH_2CH_2)_2NH_2$ | Tomah's DPA-DPG |
| $NH_2CHCH_3CH_2(OCH_2CHCH_3)_{2.6}NH_2$ | JEFFAMINE D-230 |
| $NH_2CH_2CH_2OCH_2CH_2OCH_2CH_2NH_2$ | Huntsman's XTJ-504 |
| $NH_2CCH_3CH_2(OCCH_3CHCH_2)_{2.5}(OCH_2CH_2)_{39.5}(OCH_2CHCH_3)_{2.5}NH_2$ | Huntsman's XTJ-502 |
| $NH_2CH_2CH_2OCH_2CH_2OCH_2CH_2NH_2$ | Huntsman's XTJ-504 |

Example 1

Reference

Preparation of an Etherdiamide

A 1000 mL round bottom flask equipped with a thermometer, electrical stirrer, nitrogen sweep, and a condenser, was charged with 107.22 gram of a polyetherdiamine (Tomah's DPA-DEG, Wisconsin) and 192.79 gram of undecylenic acid (Atofina, France). With the stirring off, the mixture in the flask was purged with nitrogen for 5 minutes to sweep out any oxygen in the headspace. The mixer was then turned on, and the mixture quickly turned to a light yellow color. The reaction mixture was then heated to 180° C. for 2 hours under vacuum with a nitrogen purge to strip out impurities. The reaction mixture was poured onto an aluminum lined pan and allowed to cool in air without any adverse discoloration. The melt temperature of the etherdiamide was 89° C. The acid number of the etherdiamide was 2.03.

Example 1A

Preparation of a Silicone Block Copolymer

A 1000 mL, three neck, round bottom flask equipped with a temperature probe, an electrical stirrer, and a condenser was charged with 50 grams of the etherdiamide from Example 1, and 116.52 gram of a dimethylhydrogen endblocked polydimethylsiloxane having an average degree of polymerization (DP) of 15. The contents were then heated to 140° C. for 15 minutes, then 1.03 gram of a platinum catalyst (1,3-diethenyl-1,1,3,3-tetramethyldisiloxane platinum complex in dimethyl siloxane) was added to the mixture. The mixture was allowed to react for 1 hour. The Mw of the resulting polymer was 17,200 with a polydispersity of 1.87. The melt temperature was 49° C.

Example 1-B

Preparation of a Silicone Block Copolymer

A 1000 mL, three neck round bottom flask equipped with a temperature probe, an electrical stirrer, and a condenser was charged with 37.5 grams of the etherdiamide from Example 1, and 550.5 gram of a dimethylhydrogen endblocked polydimethylsiloxane having an average DP of 100, and heated to 140° C. for 15 minutes. Then, 2.0 grams of platinum catalyst (1,3-diethenyl-1,1,3,3-tetramethyldisiloxane platinum complex in dimethyl siloxane) was added to the mixture. The mixture was allowed to react for 1 hour and then poured off. The Mw of the resulting polymer was 56,900 with a polydispersity of 2.11.

Example 2

Preparation of Etherdiamide

A 1000 mL round bottom flask equipped with a thermometer, electrical stirrer, nitrogen sweep, and a condenser, was charged with 114.61 grams of a polyetherdiamine (Huntsman's XTJ-504) and 291.4 gram of undecylenic acid (Atofina, France). With the stirring off, the mixture in the flask was purged with nitrogen for 5 minutes to sweep out any oxygen in the headspace. The mixer was then turned on, and the mixture quickly turned to a light yellow color. The reaction mixture was then heated to 180° C. for 2 hours under vacuum with a nitrogen purge to strip out impurities. The reaction mixture was poured onto an aluminum lined pan and allowed to cool in air without any adverse discoloration. The melt temperature of the etherdiamide was 94° C. The acid number as an indication of the impurities remained in the etherdiamide was 2.31.

Example 2A

Preparation of a Silicone Block Copolymer

A 1000 mL, three neck, round bottom flask equipped with a temperature probe, an electrical stirrer, and a condenser was charged with 70 grams of (etherdiamide made in Example 2), and 182.76 grams of dimethylhydrogen endblocked polydimethylsiloxane having a DP of 15. The mixture was heated to 140° C. for 15 minutes, and then 0.9 gram of platinum catalyst (1,3-diethenyl-1,1,3,3-tetramethyldisiloxane platinum complex in dimethyl siloxane) was added to the mixture. The reaction mixture was allowed to react for 1 hour and then was poured off. The Mw of the resulting polymer was 21,400 with a polydispersity of 2.14. The melt temperature was 65° C.

Example 2B

Preparation of a Silicone Block Copolymer

A 1000 mL, three neck, round bottom flask equipped with a temperature probe, an electrical stirrer, and a condenser was charged with 20 grams of (etherdiamide made in Example 2), and 294.5 grams of dimethylhydrogen endblocked polydimethylsiloxane (average 100 DP), and heated to 140° C. for 15 minutes. Then 0.91 grams of platinum catalyst (1,3-diethenyl-1,1,3,3-tetramethyldisiloxane platinum complex in dimethyl siloxane) were added to the mixture. The reaction mixture was allowed to react for 1 hour and was then poured off. The Mw of the polymer was 89,100 with a polydispersity of 3.88. The melt temperature was 74° C.

Example 3

Preparation of an Etherdiamide

A 2000 mL round bottom flask equipped with a thermometer, electrical stirrer, nitrogen sweep, and a condenser, was charged with 570.0 gram of a polyetherdiamine (Huntsman's XTJ-502) and 100.75 gram of undecylenic acid (Atofina, France). With the stirring off, the mixture in the flask was purged with nitrogen for 5 minutes to sweep out any oxygen in the headspace. The mixer was then turned on, and the mixture quickly turned to a light yellow color. The reaction mixture was then heated to 180° C. for 2 hours under vacuum with a nitrogen purge to strip out impurities. The reaction mixture was poured onto an aluminum lined pan and allowed to cool in air without any adverse discoloration. The melt temperature of the etherdiamide was 31° C. The acid number as an indication of the impurities remained in the etherdiamide was 1.88.

Example 3A

Preparation of a Silicone Block Copolymer

A 500 mL three neck round bottom flask equipped with a temperature probe, an electrical stirrer, and a condenser was charged with 100.0 gram of the etherdiamide made above in Example 3 and 112.0 g toluene, and heated to 112° C., for 15 minutes. Then 52.5 g of a dimethylhydrogen endblocked polydimethylsiloxane (average 15 DP) was then added drop wise via an addition funnel. After the addition of the first 5 grams of the siloxane, 0.83 grams of platinum catalyst (1,3-diethenyl-1,1,3,3-tetramethyldisiloxane platinum complex in dimethyl siloxane) was added to the mixture. The siloxane addition was completed and then a further 0.58 gram of catalyst was added. Following the charge of the flask, the reactants were mixed for 1 hour allowing the reaction to take place. The reaction mixture was then heated to 120° C., and vacuum was applied slowly to remove the solvent. The Mw of the resulting polymer was a bimodal distribution with 32% of the area having Mw of 13200 and polydispersity of 1.17, with the remaining 68% of the area having Mw of 2800 and polydispersity of 2.93. The melt temperature was 30° C.

Example 3B

Preparation of a Silicone Block Copolymer

A 1000 mL, three neck, round bottom flask equipped with a temperature probe, an electrical stirrer, and a condenser was charged with 40.12 gram of the etherdiamide made in Example 3 and 100.0 g of toluene, and heated to 112° C. for 15 minutes. Then, 120.05 g of a dimethylhydrogen endblocked polydimethylsiloxane (average 100 DP) was then added drop wise via an addition funnel. After the first 5 grams of the siloxane was added, 0.97 gram of platinum catalyst (1,3-diethenyl-1,1,3,3-tetramethyldisiloxane platinum complex in dimethyl siloxane) was added to the mixture. The siloxane addition was completed and then a further 1.18 gram of catalyst was added. Following the charge of the flask, the reactants were mixed for 1 hour allowing the reaction to take place. The reaction mixture was then heated to 120° C., and vacuum was applied slowly and gradually to remove the solvent. The Mw of the resulting polymer was a bimodal distribution with 75% of the area having Mw of 29700 and polydispersity of 1.54, with the remaining 25% of the area having Mw of 2800 and polydispersity of 2.93. The melt temperature was 23° C.

Example 4

Reference

Preparation of an Etherdiamide

A 1000 mL round bottom flask equipped with a thermometer, electrical stirrer, nitrogen sweep, and a condenser, was charged with 160.64 gram of a diproplylenediamine (Tomah DPA-DPG) and 244.1 gram of undecylenic acid (Atofina, France). With the stirring off, the mixture in the flask was purged with nitrogen for 5 minutes to sweep out any oxygen in the headspace. The mixer was then turned on, and the mixture quickly turned to a light yellow color as soon as the two reactants were mixed. The reaction mixture was heated to 220° C. for 1 hour under vacuum with a nitrogen purge to strip out impurities. The reaction mixture was cooled to 150° C., poured onto an aluminum lined pan, and allowed to cool in air without any adverse discoloration. The melt temperature of the etherdiamide was 30° C.

Example 4A

Preparation of a Silicone Block Copolymer

A 500 mL three neck round bottom flask equipped with a temperature probe, an electrical stirrer, and a condenser was charged with 60 gram of the etherdiamide made in Example 4 and 100 g toluene, and heated to 112° C. for 15 minutes. Then 132.5 g of a dimethylhydrogen endblocked polydimethylsiloxane (average 15 DP) was then added dropwise via an addition funnel. After the first 5 grams of the siloxane was added, 0.4 gram of platinum catalyst (1,3-diethenyl-1,1,3,3-tetramethyldisiloxane platinum complex in dimethyl siloxane) was added to the mixture. The siloxane addition was completed and then a further 0.4 gram of catalyst was added. Following the charge of the flask, the reactants were mixed for 1 hour allowing the reaction to take place. The reaction mixture was then heated to 120° C. vacuum applied slowly and gradually to remove the solvent. The Mw of the resulting polymer was 37800 and polydispersity of 3.4. The melt temperature was 25° C.

Example 5

Reference

Preparation of an Etherdiamide

A 500 mL round bottom flask equipped with a thermometer, electrical stirrer, nitrogen sweep, and a condenser, was charged with 72.02 gram of a polyetherdiamine (Huntsman's XTJ-504) and 184.79 gram of undecylenic acid (Atofina, France). With the stirring off, the mixture in the flask was purged with nitrogen for 5 minutes to sweep out any oxygen in the headspace. The mixer was then turned on and the mixture quickly turned to a light yellow color. The reaction mixture was then heated to 120° C. and maintained at temperature for 1 hour, and then increased to 180° C. for 2 hours under vacuum with a nitrogen purge to remove impurities. The reaction mixture was cooled to 150° C., poured onto an aluminum lined pan, and allowed to cool in air without any adverse discoloration. The melt temperature of the etherdiamide was 93° C. The acid number as an indication of the impurities remained in the etherdiamide was 0.28.

Example 5A

Preparation of a Silicone Block Copolymer

A 1000 mL three neck round bottom flask was equipped with a temperature probe, an electrical stirrer, and a condenser. It was charged with 6.12 gram of the etherdiamide of Example 5 made above, 7.22 grams of an etherdiamide (prepared from the reaction of JEFFAMINE D230 and undecylenic acid using the process of Example 5), 180.0 g of a dimethylhydrogen endblocked polydimethylsiloxane (average 100 dp chain), and 100.0 g of toluene, and heated to 112° C. for 15 minutes. After the first 5 grams of the siloxane was added, 0.53 gram of platinum catalyst (1,3-diethenyl-1,1,3,3-tetramethyldwasiloxane platinum complex in dimethyl siloxane) was added to the mixture. The siloxane addition was completed and then a further 0.33 gram of catalyst was added. Following the charge of the flask, the reactants are mixed for 1 hour allowing the reaction to take place. The reaction mixture was then heated to 120° C. and vacuum applied slowly and gradually to remove the solvent. The Mw of the resulting polymer was 78,200 and polydispersity of 7.24. The melt temperature was 23° C.

Example 6

Preparation of an Etherdiamide

A 500 mL round bottom flask equipped with a thermometer, electrical stirrer, nitrogen sweep, and a condenser, was charged with 72.05 gram of polyetherdiamine (Huntsman's XTJ-504) and 184.8 gram of undecylenic acid (Atofina, France). With the stirring off, the mixture in the flask was purged with nitrogen for 5 minutes to sweep out any oxygen in the headspace. The mixer was then turned on, and the mixture quickly turned to a light yellow color. The reaction mixture was then heated to 120° C. and maintained at temperature for 1 hour, and then to 180° C. for 2 hours under vacuum with a nitrogen purge to strip out impurities. The reaction mixture was cooled to 150° C., poured onto an aluminum lined pan, and allowed to cool in air without any adverse discoloration. The melt temperature of the etherdiamide was 93° C. The acid number as an indication of the impurities remained in the etherdiamide was 2.8.

Example 6A

Preparation of a Silicone Block

A 1000 mL three neck round bottom flask equipped with a temperature probe, an electrical stirrer, and a condenser was charged with 24.99 gram of the etherdiamide from Example 6, 23.65 grams of DC 8337 (a diamide functional siloxane, Dow Corning Corporation, Midland Mich.) and 100.0 g toluene, and heated to 112° C. for 15 minutes. Then 154.02 g of a dimethylhydrogen endblocked polydimethylsiloxane (average 15 DP chain) was added dropwise via an addition funnel. After the first 5 grams of the siloxane was added, 0.38 gram of platinum catalyst (1,3-diethenyl-1,1,3,3-tetramethyldisiloxane platinum complex in dimethyl siloxane) was added to the mixture. The siloxane addition was completed and then a further 0.32 gram of catalyst was added. Following the charge of the flask, the reactants were mixed for 1 hour allowing the reaction to take place. The reaction mixture was then heated to 120° C. and vacuum applied slowly and gradually to remove the solvent. The Mw of the resulting polymer was 47,500 and polydispersity of 3.59. The melt temperature was 86.5 C.

Example 7

Preparation of a Silicone Block Copolymer

A 1000 mL, three neck, round bottom flask equipped with a temperature probe, an electrical stirrer, and a condenser was charged with 12.5 gram of the etherdiamide from Example 6, 35.55 grams of DC 8337 diamide siloxane and 50.0 g toluene, and heated to 112° C., for 15 minutes. Then 154.02 g of a dimethylhydrogen endblocked polydimethyl siloxane (average 15 DP chain) was added dropwise via an addition funnel. After the first 5 grams of the siloxane was added, 0.38 gram of platinum catalyst (1,3-diethenyl-1,1,3,3-tetramethyldisiloxane platinum complex in dimethyl siloxane) was added to the mixture. The siloxane addition was completed and then a further 0.32 gram of catalyst was added. Following the charge of the flask, the reactants were mixed for 1 hour allowing the reaction to take place. The reaction mixture was then heated to 120° C. and vacuum applied slowly and gradually to remove the solvent. The Mw of the resulting polymer was 39,600 and polydispersity of 3.55. The melt temperature was 94.0° C.

Example 8

Preparation of a Silicone Block Copolymer

A 1000 mL three neck round bottom flask equipped with a temperature probe, an electrical stirrer, and a condenser was charged with 150 grams of etherdiamide as prepared in Example 1, and 349.56 gram of a dimethylhydrogen endblocked polydimethylsiloxane (average 15 DP chain) and heated to 140° C. for 15 minutes. Then 3.01 gram of platinum catalyst (1,3-diethenyl-1,1,3,3-tetramethyldisiloxane platinum complex in dimethyl siloxane) was added to the mixture. The reaction mixture was allowed to react for 1 hour to build molecular weight and was poured off. The Mw of the polymer was 19,200 with a polydispersity of 1.55.

Example 9

Preparation of a Silicone Block Copolymer

A 1000 mL three neck round bottom flask equipped with a temperature probe, an electrical stirrer, and a condenser was charged with 120 gram of the etherdiamide made in Example 3 and 300.0 g of isopropyl alcohol, and heated to 80° C. for 15 minutes. Then 120.05 g of a dimethylhydrogen endblocked polydimethylsiloxane (average 100 DP chain) was added dropwise via an addition funnel. After the first 5 grams of the siloxane was added, 2 gram of platinum catalyst (1,3-diethenyl-1,1,3,3-tetramethyldisiloxane platinum complex in dimethyl siloxane) was added to the mixture. The siloxane addition was completed and then a further 2 gram of catalyst was added. Following the charge of the flask, the reactants are mixed for 1 hour allowing the reaction to take place. The reaction mixture was then heated to 120° C., and vacuum applied slowly and gradually to remove the solvent. The Mw of the resulting polymer was a bimodal distribution with 48% of the area having Mw of 21,500 and polydispersity of 1.48, with the remaining 52% of the area having Mw of 3950 and polydispersity of 1.09. The melt temperature was 23° C.

Example 10

Preparation of Gels with the Silicone Block Copolymers

These examples illustrate the ability of the silicone block copolymers of the present invention to form gels with a variety of cosmetic emollients. The silicone block copolymers described in examples 1-6 were used to prepare gels by weighing equal amounts (5-7 g of each) of the silicone block copolymer and the cosmetic emollient into a ½ ounce glass vial and placing the vial on a hot plate set for approximately 70° C. If the silicone block copolymer did not melt at 70° C., then the hot plate temperature was increased to as high as 100° C. to melt the silicone block copolymer. The mixture of silicone block copolymer and cosmetic emollient was not heated above the temperature needed to melt the silicone block copolymer. After silicone block copolymer had melted, the glass vial containing mixture of silicone block copolymer and cosmetic emollient was mixed briefly on a vortex mixer and then allowed to cool. The quality of the gel was rated after the mixture had cooled to room temperature. The gel quality was assigned a rating according to the following scheme, where A represents the best gel.

| Rating | Description |
| --- | --- |
| A | Firm clear gel (able to read 12 point type through vial of gel) |
| B | Firm translucent gel (unable to read 12 point type through vial of gel) |
| C | Firm gel, but hazy |
| D | Firm opaque gel |
| E | Clear to hazy soft gel (flows when vial is tipped) |
| F | No gel - emollient separates from silicone block copolymer |

For comparison purposes, a commercial silicone block copolymer that is sold as Dow Corning® 2-8179 Gellant (INCI Name Nylon-611/Dimethicone Copolymer) was included in the evaluation of the silicone block copolymers of the present invention.

TABLE 1

Evaluation of silicone block copolymers in silicones, isododecane, and non-polar (long chain) ester emollients

| Silicone block copolymer | Dimethicone (10 cSt) | Cyclopentasiloxane | Isododecane | Isononyl Isononanoate | Isopropyl Palmitate | Isopropyl Myristate |
|---|---|---|---|---|---|---|
| 2-8179 | B | B | B | B | B | B |
| 1-A | F | C | B | F | B | B |
| 1-B | A | E | E | E | E | E |
| 2-A | F | F | A | A | E | A |
| 2-B | E | E | B | F | A | A |
| 3-A | F | D | D | F | C | F |
| 3-B | F | F | E | E | E | E |
| 4 | F | E | E | E | E | E |
| 5 | F | F | E | E | E | E |
| 6 | F | F | B | B | B | B |
| 7 | F | F | A | A | A | A |
| 8 | C | E | B | E | B | B |
| 9 | E | F | F | F | C | C |

TABLE 2

Evaluation of silicone block copolymers in polar (short chain) ester emollients

| Silicone block copolymer | PPG-3 Myristyl Ether | Octyl Pelargonate | Propylene Glycol Dipelargonate | Octyl Isononanoate |
|---|---|---|---|---|
| DC 2-8179 | F | B | F | B |
| 1-A | B | B | B | B |
| 1-B | F | E | F | E |
| 2-A | B | A | A | A |
| 2-B | F | A | C | A |
| 3-A | D | C | D | D |
| 3-B | F | E | F | E |
| 4 | E | E | E | E |
| 5 | F | E | F | E |
| 6 | B | B | B | B |
| 7 | B | A | A | A |
| 8 | B | C | C | C |
| 9 | F | C | F | F |

TABLE 3

Evaluation of silicone block copolymers in sunscreen oils

| Silicone block copolymer | Ethylhexyl Methoxycinnamate (Octinoxate) | Ethylhexyl Salicylate (Octisalate) | Octocrylene |
|---|---|---|---|
| DC 2-8179 | F | D | F |
| 1-A | B | B | D |
| 1-B | F | F | F |
| 2-A | C | C | C |
| 2-B | F | C | F |
| 3-A | E | F | E |
| 3-B | B | E | E |
| 4 | F | E | F |
| 5 | F | E | F |
| 6 | E | B | E |
| 7 | E | B | E |
| 8 | B | B | C |
| 9 | E | F | F |

Example 11

Preparation of Stick Formulations

To illustrate the utility the silicone block copolymers to prepare various types of stick formulations, the following formulations were prepared.

| Sunscreen Stick | | |
|---|---|---|
| Ingredient | Wt. % | Trade name (supplier) |
| Silicone block copolymer of Example 6 | 50.0 | |
| Ethylhexyl Salicylate (Octisalate) | 20.0 | Escalol 587 (International Specialty products) |
| Ethylhexyl Methoxycinnamate (Octinoxate) | 10.0 | Escalol 557 (International Specialty products) |
| Tridecyl Neopentanoate | 10.0 | Trivent NP-13 (Trivent) |
| Propylene Glycol Dipelargonate | 10.0 | Jeechem PGDP (Jeen International Corporation) |

This formulation was prepared by melting all of the ingredients together (at ~80° C.) in a suitable container and mixing until uniform. The molten mixture was then poured into molds and allowed to cool.

| Color Cosmetic Stick | | |
|---|---|---|
| Ingredient | Wt. % | Trade name (supplier) |
| Silicone block copolymer of Example 3-A | 55.9 | |
| PPG-3 Myristyl Ether | 9.2 | Jeechem PMA-3 (Jeen International Corporation) |
| Isopropyl Myristate | 9.2 | Jeechem IPM-NF (Jeen International Corporation) |
| Isononyl Isononanoate | 9.2 | Pelemol IN-2 (Phoenix Chemical, Inc.) |
| Propylene Glycol Dipelargonate | 5.5 | Jeechem PGDP (Jeen International Corporation) |
| PEG-150 Dibehenate | 7.4 | Ethox P-6000 DB (Ethox Chemicals, Inc.) |

-continued

Color Cosmetic Stick

| Ingredient | Wt. % | Trade name (supplier) |
|---|---|---|
| Calcium Sodium Borosilicate (and) and Iron Oxides | 1.8 | Reflecks Dimensions Really Rouge (Engelhard Corporation) |
| Calcium Sodium Borosilicate (and) and Iron Oxides | 1.8 | Reflecks Dimensions Clearly Copper Rouge (Engelhard Corporation) |

This formulation was prepared by melting all of the ingredients (at ~80° C.) except for the pigments (Calcium Sodium Borosilicate and Iron Oxides) together in a suitable container and mixing until uniform. The pigments were then stirred into the molten mixture and the formulation was again mixed until uniform. Then the molten formulation was poured into molds and allowed to cool. The pigments used in this example provide a red color on the skin. Other types of pigment particles can be used to provide other colors and various optical effects. Oil-soluble dyes can also be used to provide a transparent color effect on the skin.

High Gloss Color Cosmetic Gel

| Ingredient | Wt. % | Trade name (supplier) |
|---|---|---|
| Dimethicone/Vinyl Dimethicone Crosspolymer (and) Water (and) C12-14 Pareth-12 | 22.7 | Dow Corning ® 9509 Silicone Elastomer Suspension (Dow Corning) |
| Dimethicone | 29.0 | Dow Corning ® 200 Fluid/350 cSt (Dow Corning) |
| Silicone block copolymer of Example 1-B | 3.4 | |
| Isononyl Isononanoate | 1.2 | Pelemol IN-2 (Phoenix Chemical, Inc.) |
| Dimethicone (and) Trimethylsiloxysilicate | 2.7 | Dow Corning ® 593 Fluid (Dow Corning) |
| Dimethicone (and) Dimethiconol | 9.1 | Dow Corning ® 1503 Fluid (Dow Corning) |
| Hydrogenated Polyisobutene (and) Ethylene/Propylene/Styrene Copolymer (and) Butylene/Ethylene/Styrene Copolymer | 29.6 | Versagel ME 750 (Penreco) |
| Calcium Sodium Borosilicate (and) and Iron Oxides | 0.9 | Reflecks Dimensions Really Rouge (Engelhard Corporation) |
| Calcium Sodium Borosilicate (and) and Iron Oxides | 0.9 | Reflecks Dimensions Blazing Bronze Rouge (Engelhard Corporation) |
| Fragrance | 0.5 | 1511 Peach (Bell-Aire Fragrances) |

This formulation was prepared by combining the first two ingredients and heating to ~70° C. The next two ingredients were then heated to ~70° C. and mixed until uniform, then combined with the previous mixture. The mixture was then cooled room temperature while continuing to mix. The remaining ingredients were added in the order listed and mixed well after each addition. The pigments used in this example provide a high gloss film and an orange color on the skin. Other types of pigment particles can be used to provide other colors and various optical effects. Oil-soluble dyes can also be used to provide a transparent color effect on the skin.

Antiperspirant Stick

| Ingredient | Wt. % | Trade name (supplier) |
|---|---|---|
| Silicone block copolymer of Example 7 | 50.0 | |
| Aluminum Zirconium Tetrachlorohydrex GLY (and) Propylene Glycol | 30.0 | Reach AZP 908 PG30 (Reheis, Inc.) |
| Propylene Glycol Dipelargonate | 10.0 | Jeechem PGDP (Jeen International Corporation) |
| Isononyl Isononanoate | 10.0 | Pelemol IN-2 (Phoenix Chemical, Inc.) |

This formulation was prepared by melting all of the ingredients together (at ~80° C.) in a suitable container and mixing until uniform. The molten mixture was then poured into molds and allowed to cool.

Example 12

Silicone Block Copolymers in Emulsions

The silicone block copolymers, having non-polar (silicone) and polar (polyether) blocks, can exhibit surfactant like behavior such as emulsification. A simple screening test was devised demonstrate emulsification performance whereby 10 parts of the silicone block copolymer was combined with 10 parts of a cosmetic emollient and heated to 80° C. One part of a cosmetic thickener (Sepigel 305, manufactured by SEPPIC) was added to the hot mixture and mixed well. This mixture was rapidly added to 79 parts of water that had been heated to 80° C. while stirring vigorously. The mixture was allowed to cool to room temperature with continuous stirring. After the mixture was cool, it was allowed to stand for several hours and the quality of the emulsion was rated according to the following scales:

| Rating | Description |
|---|---|
| 1 | Stable emulsion |
| 2 | Emulsion with creaming |
| 3 | No emulsion |

For comparison purposes, a commercial silicone block copolymer that is sold as Dow Corning® 2-8179 Gellant (INCI Name Nylon-611/Dimethicone Copolymer) was included in the evaluation of the silicone block copolymers of the present invention.

TABLE 4

Evaluation of emulsification of silicone block copolymers mixed with isododecane and non-polar (long chain) ester emollients

| Silicone block copolymer | Isododecane | Isononyl Isononanoate | Isopropyl Palmitate | Isopropyl Myristate |
|---|---|---|---|---|
| 2-8179 | 3 | 3 | 3 | 3 |
| 1-B | 2 | 3 | 1 | 3 |
| 2-A | 3 | 1 | 1 | 1 |
| 2-B | 2 | 1 | 1 | 1 |
| 3-A | 1 | 3 | 1 | 1 |
| 4 | 2 | 3 | 3 | 1 |
| 8 | 2 | 1 | 1 | 1 |
| 9 | 2 | 1 | 1 | 1 |

TABLE 5

Evaluation of silicone block copolymers
in polar (short chain) ester emollients

| Silicone block copolymer | PPG-3 Myristyl Ether | Octyl Pelargonate | Propylene Glycol Dipelargonate | Octyl Isononanoate |
|---|---|---|---|---|
| 2-8179 | 3 | 3 | 3 | 1 |
| 1-B | 1 | 1 | 1 | 1 |
| 2-A | 1 | 1 | 1 | 1 |
| 2-B | 3 | 1 | 1 | 3 |
| 3-A | 1 | 1 | 1 | 1 |
| 4 | 1 | 1 | 1 | 3 |
| 8 | 3 | 1 | 1 | 1 |
| 9 | 1 | 1 | 1 | 1 |

In an emulsion, the silicone block copolymers do not provide an appreciable gellation effect, but they do contribute other effects such as film formation and a novel skin feel on the skin and hair.

Example 13

Use of Emulsified Silicone Block Copolymers in Formulations

Sunscreen Lotion

| Ingredient | Wt. % | Trade name (supplier) |
|---|---|---|
| PART A | | |
| Bis-Hydroxyethoxypropyl Dimethicone | 7.0 | Dow Corning ® 5562 Carbinol Fluid (Dow Corning) |
| Lauryl PEG/PPG-18/18 Methicone | 6.0 | Dow Corning ® 5200 Formulation Aid (Dow Corning) |
| Silicone block copolymer of Example 9 | 2.0 | |
| PPG-3 Myristyl Ether | 1.0 | Jeechem PMA-3 (Jeen International Corporation) |
| Cyclopentasiloxane | 6.0 | Dow Corning ® 245 Fluid (Dow Corning) |
| Ethylhexyl Methoxycinnamate (Octinoxate) | 7.5 | Escalol 557 (International Specialty products) |
| PART B | | |
| Water | 65.1 | |
| Glycerin | 3.0 | |
| Sodium Chloride | 2.0 | |
| DM DM Hydantoin | 0.4 | Glydant (Lonza, Inc.) |

This formulation was made by combining the silicone block copolymer and the PPG-3 myristyl ether and warming to 70° C. The remaining ingredients for Part A were warmed to 70° C. and combined with the silicone block copolymer and PPG-3 myristyl ether in a mixing vessel that was large enough to contain the entire batch with extra room to allow for vigorous mixing. Part A was mixed until uniform and allowed to cool to room temperature. The ingredients for Part B were added to a separate container and mixed until a homogeneous solution was obtained. Part B was then slowly added to Part A while mixing at high speed using an agitator that provided turbulent mixing. After all of Part B was added, the emulsion was mixed at high speed for 10 minutes.

Hair Conditioning and Styling Gel

| Ingredient | Wt. % | Trade name (supplier) |
|---|---|---|
| PART A | | |
| Water | 86.2 | |
| Xanthan Gum | 0.2 | Keltrol T (C.P. Kelco) |
| DM DM Hydantoin | 0.1 | Glydant (Lonza, Inc.) |
| PART B | | |
| Silicone block copolymer of Example 8 | 4.0 | |
| Cyclopentasiloxane | 3.0 | Dow Corning ® 245 Fluid (Dow Corning) |
| PART C | | |
| Polyquaternium-10 | 0.1 | Ucare Polymer JR-30M (Amerchol) |
| PART D | | |
| Cyclopentasiloxane (and) Dimethiconol | 2.5 | Dow Corning ® 1501 Fluid (Dow Corning) |
| Polyacrylamide (and) C13-14 Isoparaffin (and) Laureth-7 | 2.5 | Sepigel 305 (SEPPIC) |
| Fragrance | 0.4 | Halo (Firmenich) |
| PART E | | |
| Sea Kelp Extract | 0.5 | Sea Kelp Extract (Bell Flavors & Fragrance) |
| Hydrolyzed Vegetable Protein PG-Propyl Silanetriol | 0.5 | Keravis (CRODA, Inc.) |

This formulation was prepared by combining the ingredients for Part A in a vessel that was large enough to hold the entire batch with extra room to allow for mixing. Part A was mixed and warmed to 75° C. The ingredients for Part B were combined in a small container and warmed to 75° C., mixed until uniform, and then added to Part A. The resulting emulsion was cooled to room temperature with continued mixing. Part C was added slowly with sufficient mixing to rapidly incorporate the powder into the batch. Next, the ingredients for Part D were mixed together and added to the batch with vigorous mixing. The mixing speed was increased as the batch thickened to maintain good agitation. Finally, the ingredients for Part E were added to the batch and the batch was mixed until uniform.

Light Conditioning Shampoo

| Ingredient | Wt. % | Trade name (supplier) |
|---|---|---|
| PART A | | |
| Water | 51.9 | |
| Sodium Laureth Sulfate | 33.0 | Rhodaplex ES-2 (Rhodia, Inc..) |
| Cocamidopropyl Betaine | 3.0 | Jeeteric CAB-L (Jeen International Corporation) |
| Cocamide DEA | 3.0 | Incromide CA (CRODA, Inc.) |
| DM DM Hydantoin | 0.1 | Glydant (Lonza, Inc.) |
| PART B | | |
| Silicone block copolymer of Example 2-B | 2.5 | |
| Octyl Pelargonate | 2.5 | Jeechem OPG (Jeen International Corporation) |

-continued

Light Conditioning Shampoo

| Ingredient | Wt. % | Trade name (supplier) |
|---|---|---|
| PART C | | |
| Polyquaternium-47 | 1.0 | Merquat 2001 (Nalco Company) |
| PART D | | |
| Polyacrylamide (and) C13-14 Isoparaffin (and) Laureth-7 | 2.0 | Sepigel 305 (SEPPIC) |
| Fragrance | 1.0 | Fresh Wave (Mane) |

This formulation was prepared by combining the ingredients for Part A into a suitable mixing vessel and heating to 80° C. The ingredients for Part B were combined in a small mixing vessel, heated to 80° C., and mixed until uniform. Part B was then added to Part A while mixing vigorously. The resulting mixture was then cooled to room temperature with continued mixing. Part C was then added and mixed until this ingredient was uniformly dispersed into the batch. Finally, the ingredients for Part D were added and the mixing speed was increased as the batch thickened to maintain good agitation and the batch was mixed until uniform.

The invention claimed is:

1. A process for making a silicone block copolymer comprising;
   I) reacting an omega-olefinic carboxylic acid selected from the group consisting of undecylenic acid, acrylic acid, 3-butenoic acid, and pentenoic acid with poly(oxyethylene)diamine or poly(oxypropylene)diamine or mixtures thereof to form a diamide,
   II) reacting the diamide and an alpha-omega olefin with an SiH containing siloxane having the average structure

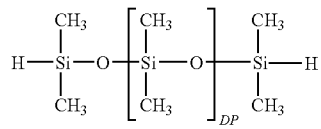

wherein DP is an integer having a value of 1-500 to form the silicone block copolymer.

2. The process of claim 1 wherein the diamide, the alpha-omega olefin, and the SiH containing siloxane are reacted via a platinum catalyzed hydrosilylation.

3. The process of claim 1 wherein the alpha-omega olefin has the formula $H_2C=CH-A-CH=CH_2$, where A is a divalent organic group or organopolysiloxane.

4. The process of claim 3 wherein A is a divalent organic group selected from linear or branched $C_1$-$C_{30}$ alkylene chains.

5. The process of claim 4 wherein the alpha-omega olefin is 1,5 hexadiene.

6. A silicone block copolymer prepared by the process of claim 1.

7. A personal, household, or healthcare composition comprising the silicone block copolymer of claim 6.

8. The personal care composition of claim 7 wherein the personal care composition is in the form of a stick, gel, or lotion.

9. A gel comprising the composition of claim 6 and an oil.

10. The gel of claim 9 wherein the oil is an organic or silicone oil.

11. An emulsion comprising the composition of claim 6.

* * * * *